(12) United States Patent
Wind

(10) Patent No.: US 8,337,770 B2
(45) Date of Patent: Dec. 25, 2012

(54) UV LIGHT WRITING INSTRUMENT STERILIZER

(76) Inventor: Brian E. Wind, North Canton, OH (US)

( * ) Notice: Subject to any disclaimer, the term of this patent is extended or adjusted under 35 U.S.C. 154(b) by 1130 days.

(21) Appl. No.: 12/001,388

(22) Filed: Dec. 11, 2007

(65) Prior Publication Data

US 2009/0148358 A1 Jun. 11, 2009

(51) Int. Cl.
*B01J 19/08* (2006.01)

(52) U.S. Cl. .... 422/186.3; 422/22; 422/24; 250/455.11; 250/461.1

(58) Field of Classification Search ............... 422/186.3, 422/22, 24; 250/455.11, 461.1
See application file for complete search history.

(56) References Cited

U.S. PATENT DOCUMENTS

| | | |
|---|---|---|
| 3,519,166 A | 7/1970 | Yingst et al. |
| 3,954,407 A | 5/1976 | Andary et al. |
| 4,174,787 A | 11/1979 | Merila |
| 4,227,626 A | 10/1980 | Merila |
| 4,669,617 A | 6/1987 | Boeckmann et al. |
| 4,789,081 A | 12/1988 | Mobbs |
| 4,806,770 A | 2/1989 | Hylton et al. |
| 4,868,397 A | 9/1989 | Tittel |
| 4,888,487 A | 12/1989 | Ritter |
| 4,973,847 A | 11/1990 | Lackey et al. |
| 5,023,460 A | 6/1991 | Foster, Jr. et al. |
| 5,029,252 A | 7/1991 | Ameseder |
| 5,126,572 A | 6/1992 | Chu |
| 5,185,532 A | 2/1993 | Zabsky et al. |
| 5,487,877 A | 1/1996 | Choi |
| 5,641,464 A | 6/1997 | Briggs, III et al. |
| 5,683,655 A | 11/1997 | Carter |
| 5,720,742 A * | 2/1998 | Zacharias ................... 606/1 |
| 5,743,430 A | 4/1998 | Freixas |
| 5,892,233 A | 4/1999 | Clement |
| 5,920,075 A | 7/1999 | Whitehead |
| 5,960,988 A | 10/1999 | Freixas |
| 6,039,928 A | 3/2000 | Roberts |
| 6,090,346 A | 7/2000 | Rose et al. |
| 6,132,784 A | 10/2000 | Brandt et al. |
| 6,461,568 B1 | 10/2002 | Eckhardt |
| 7,213,603 B2 | 5/2007 | Pinsky |
| 7,247,865 B2 | 7/2007 | Flores et al. |
| 7,250,145 B1 | 7/2007 | Miller |
| 7,348,572 B2 | 3/2008 | Shin |
| 7,642,524 B1 * | 1/2010 | Alvarez et al. ........... 250/455.11 |
| 7,646,000 B2 | 1/2010 | Shih |
| 2002/0168287 A1 | 11/2002 | Eckhardt et al. |
| 2003/0000902 A1 | 1/2003 | Keis et al. |
| 2005/0031485 A1 * | 2/2005 | Wen ............................. 422/28 |

(Continued)

OTHER PUBLICATIONS

UV Irradiation Dosage Table.

(Continued)

*Primary Examiner* — Xiuyu Tai

(57) ABSTRACT

A writing instrument sterilization device having an automatic dispensing delivery mechanism for recycling multiple writing instruments and automatically delivering a single sterilized writing instrument on demand. The writing instrument sterilizer is comprised of a housing having a collection aperture for receiving at least one writing instrument and a discharge aperture for dispensing the writing instrument. The writing instrument is conveyed on track that is disposed within the housing and extends between the collection aperture and the discharge aperture. A UV illumination source sterilizes the writing instrument by emitting radiation to the surface of the writing instrument. An automatic dispensing delivery mechanism is provided to move an ejector member from a first writing instrument receiving position to a second writing instrument dispensing position.

23 Claims, 7 Drawing Sheets

U.S. PATENT DOCUMENTS

| | | | |
|---|---|---|---|
| 2005/0230638 A1 | 10/2005 | Ancona et al. | |
| 2005/0236579 A1 | 10/2005 | Jenkins et al. | |
| 2005/0254992 A1 | 11/2005 | Jenkins et al. | |
| 2006/0216193 A1 | 9/2006 | Johnson et al. | |
| 2006/0255291 A1 | 11/2006 | Harris | |
| 2008/0199353 A1* | 8/2008 | Mlodzinski et al. | 422/24 |
| 2010/0061887 A1 | 3/2010 | Harper et al. | |
| 2010/0143188 A1 | 6/2010 | Roiniotis | |
| 2011/0079732 A1 | 4/2011 | Kreitenberg | |

OTHER PUBLICATIONS

Antimicrobial efficacy and potential application of a newly developed plasma-based ultraviolet irradiation facility, Journal of Hospital Infection (2003) 55, 204-211.

Disinfection Using Ultraviolet Radiation as an Antimicrobial Agent: A Review and Synthesis of Mechanisms and Concerns. Piluso & Moffatt-Smith PDA Journal of Pharmaceutical Science.

Comparative Inactivation of Adenovirus Serotypes by UV Light Disinfection, Nwachuku, Gerba, Oswald & Mashadi. Applied and Environmental Microbiology, Sep. 2005 p. 5633-5636.

UV Light Technology Limited.

American Air & Water—UV Lamps—UV Lamp Types.

Lenntech FAQ's UV.

A Primer on UV-C Light.

Physical Sterilization and Disinfection, Blatchley III & Peel, p. 823-851.

American Ultraviolet Company—Determining Ultraviolet Intensities Using Germicidal Lamps.

* cited by examiner

UV LIGHT WRITING INSTRUMENT STERILIZER

BACKGROUND OF THE INVENTION

1. Field of the Invention

The present invention relates generally to sterilization and dispensing devices for writing instruments, and more particularly to an Ultra Violet Light writing instrument sterilizer and dispenser including a mechanism for recycling multiple writing instruments and automatically delivering a single sterilized writing instrument on demand.

2. Description of the Related Art

Hand-held writing devices are commonly utilized and shared by individuals in public places such as hospitals, doctor's offices, banks, department stores, and restaurants. Infectious microorganisms including viruses and bacteria colonize on these writing devices and promote the spread of communicable diseases from the common cold to more serious infections. The use of ultraviolet light for its purification and germicidal effects is well known. When administered at the desired frequencies, durations, and intensities, ultraviolet light is able to kill a wide spectrum of microorganisms.

SUMMARY OF THE INVENTION

An object of the present invention is to provide a writing instrument sterilization device having an automatic dispensing delivery system. The delivery system may be configured for sterilizing and recycling multiple writing instruments simultaneously and automatically delivering for use a single sterile writing instrument. This objective is to provide multiple end users with a recyclable sterilized writing device to diminish the spread of communicable diseases.

An ultraviolet (UV) irradiating light device that emits ultraviolet radiation in a range sufficient to eradicate bacteria, viruses, and other pathogens and microorganisms may be employed for a predetermined period of time to sterilize the writing instrument.

Another aspect of this invention is to deliver a writing instrument in a touch-less manner in order to limit the exposure to germs inherent on a person's hand. When a writing device is placed into the dispenser, a switch may be automatically triggered to start a UV light sterilization process. In this manner, energy can be conserved because the writing instrument sterilizer is not superfluously being operated.

The amount of UV light required to sterilize one or more writing instruments within the dispenser is a function of the intensity of the UV light (microwatts), the time period that the UV light is emitting UV light onto the instrument being sterilized, and the area over which the UV light is intended to sterilize.

According to another aspect of this invention, a writing instrument will not be delivered from the housing of the writing instrument sterilizer until after the writing instrument has been exposed to the UV light for a minimum period of time and the writing instrument is completely sterilized.

Another aspect of this invention is to construct an internal track to carry the writing instruments through the writing instrument sterilizer such that the outer construction of the track does not prevent the UV light from emitting onto all surfaces of the writing instrument.

Furthermore, the inner walls of the writing instrument sterilizer are laminated, covered, or coated with a reflective material to enhance the sterilization process by reflecting the UV light from the walls of the housing back to the writing instruments for irradiation and sterilization. After the writing instrument to be discharged from the writing instrument sterilizer has been sterilized by the minimal UV dosage, a dispensing assembly is automatically activated and the writing instrument is dispensed on demand from the writing instrument sterilizer.

Yet, in accordance with another aspect of this invention, various sensors and/or detection devices may be connected in a control circuit to a processor that would issue instructions to initiate the irradiation and/or sterilization process through activation of the UV light and/or concurrent instructions to dispense the writing instrument after it has been sterilized. Some of the devices providing input information to a controller to the writing instrument sterilizer may include, but is not limited to, an input switch, a dispensing switch, a contamination sensor and an illumination switch.

The UV activation or input sensor may be located at a writing instrument entry port, such as a collection opening. The input sensor may be embodied as a mechanical switch or a motion sensor that detects a motion in close proximity to the collection opening and/or input sensor (such as a hand waving motion). The activation of the switch or input sensor would send a control signal that would be routed via a power source to the UV light and/or timer to supply power to the lamp for a period of time. The present invention also has the ability to prevent the discharge of a writing instrument until the writing instrument to be discharged has been through the sterilization process for at least the minimum UV light exposure time required for sterilization.

The discharge sensor may be located at a writing instrument discharge or exit port, such as a dispensing opening. The discharge sensor may be embodied as a mechanical switch or motion sensor that detects a motion in close proximity to the dispensing opening or dispensing sensor (such as a hand waving motion). The discharge sensor could then send a control signal that would be routed via a power source to the dispensing assembly to discharge a sterile writing instrument from the writing instrument sterilizer.

Still another object of the present invention is to construct the writing instrument sterilizer so that the user can only touch one sterile writing instrument delivered through a discharge opening at a time and not any of the other sterile writing instruments stored within the housing of the writing instrument sterilizer. This invention is versatile and may be expanded into other technologies requiring sterilization, such as for a writing stylus for a PDA, a credit transaction point of sale (POS) terminal, a kiosk or similar system. This invention is also useful for a variety of other portable hand held devices.

These and other objects, features, and/or advantages may accrue from various aspects of embodiments of the present invention, as described in more detail below.

BRIEF DESCRIPTION OF THE DRAWINGS

Various exemplary embodiments of this invention will be described in detail, wherein like reference numerals refer to identical or similar components or steps, with reference to the following figures, wherein.

DETAILED DESCRIPTION OF EXEMPLARY EMBODIMENTS

Figure 1:
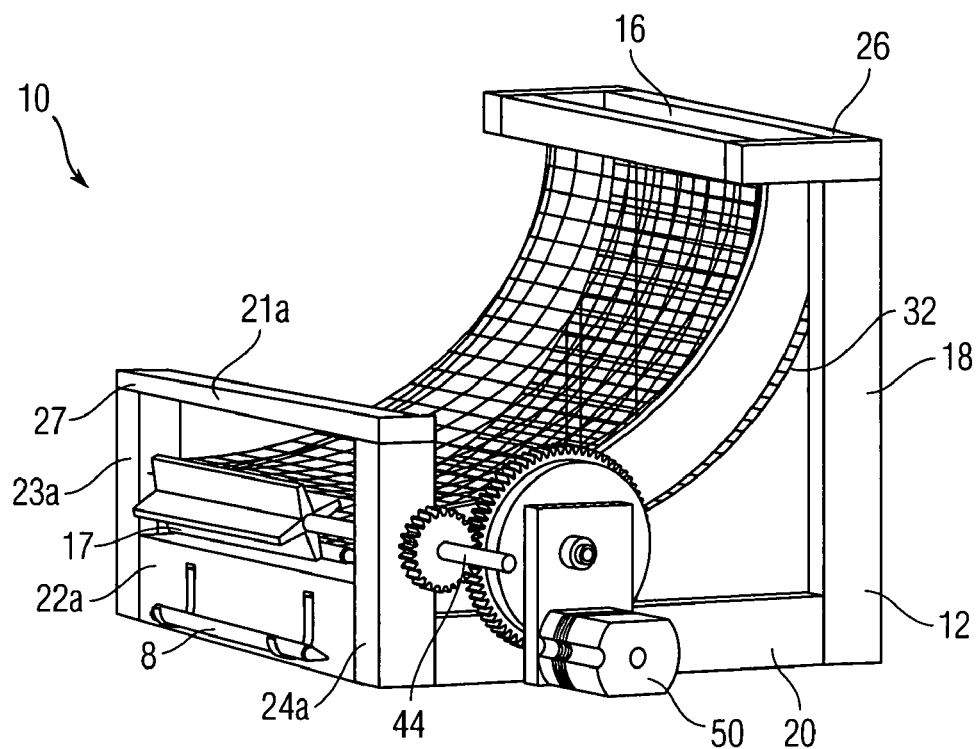
FIG. 1 illustrates a perspective view of the device in accordance with this invention.

Particular embodiments of the present invention will now be described in greater detail with reference to the figures. Like reference numerals apply to similar parts throughout the several views.

This invention overcomes the conventional problems described above by providing a UV light writing instrument sterilizer sanitizer and dispenser sterilization and dispensing device FIG. 1 illustrates a writing instrument sterilizer 10 for sanitizing a writing instrument 8. The writing instrument sterilizer 10 is comprised of a structural frame 12 including a collection opening 16 and a discharge opening 17. The collection opening 16 is connected to the discharge opening 17 by a pair of vertical support members 18 connected to a pair of base support members 20.

As shown, the discharge opening 17 is defined by a discharge frame 27 and configured with an elongated shape through which a writing instrument 8 may be dispensed. The elongated discharge opening 17 may be defined rectangular in shape to include an upper longitudinal member 21a, a lower longitudinal member 22a, and a pair of side members 23a, 24a.

Figure 2:
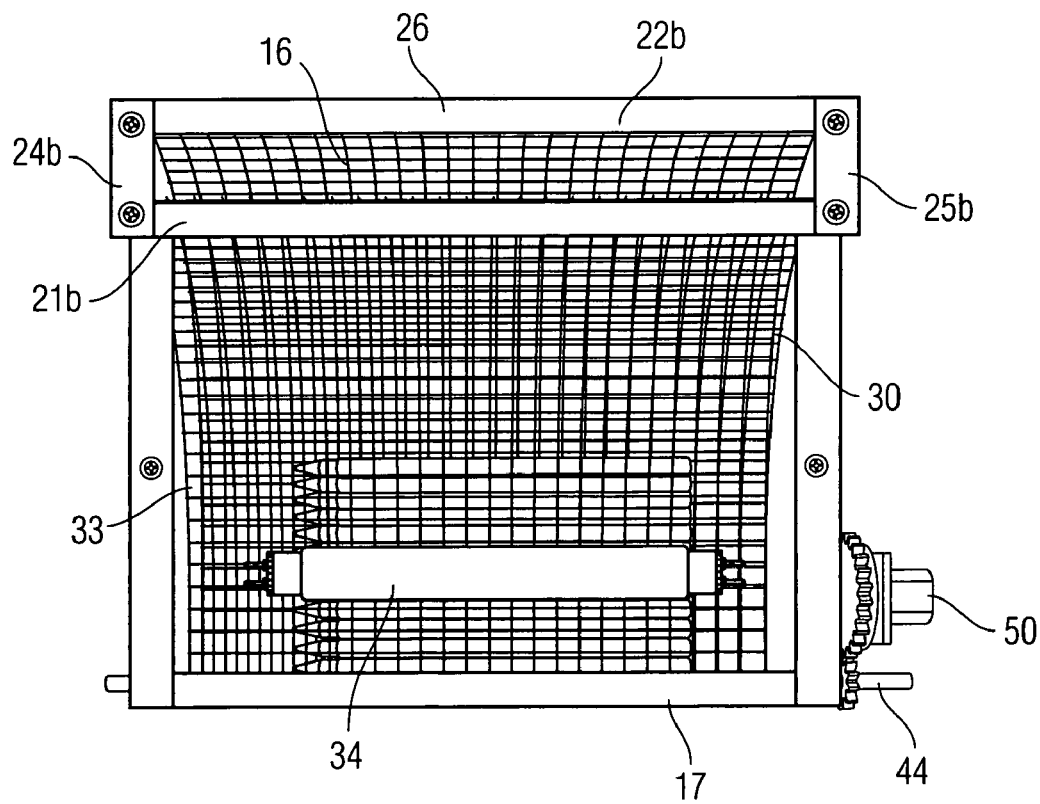
FIG. 2 illustrates a top view of the device in accordance with this invention.
Figure 3:
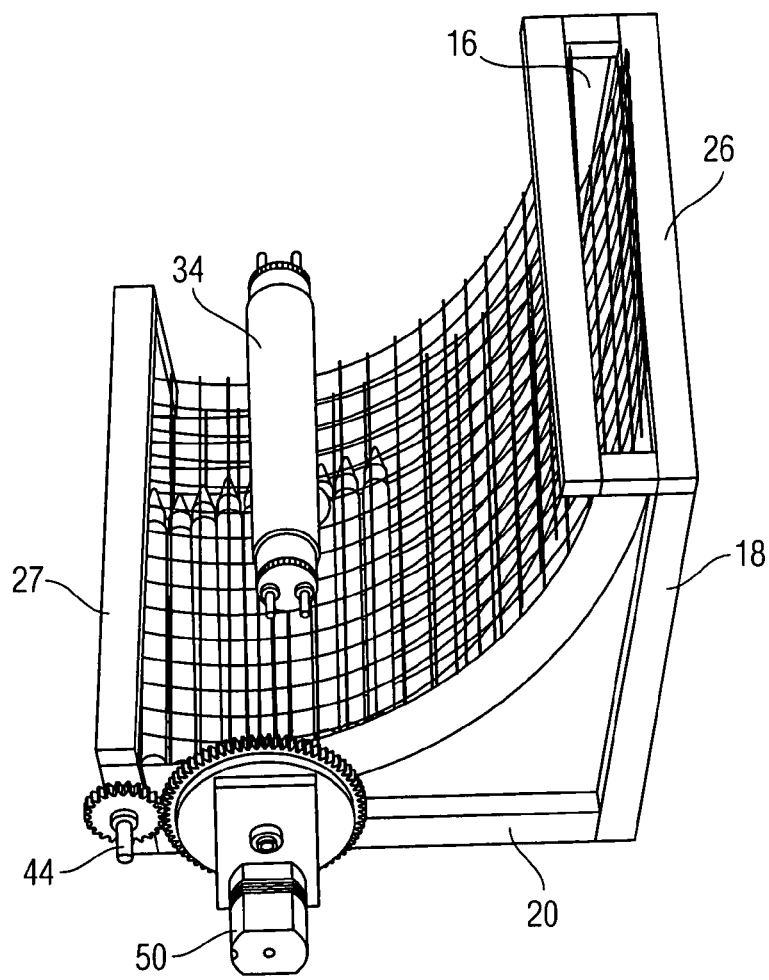
FIG. 3 illustrates a side view of the device in accordance with this invention.
Figure 4:
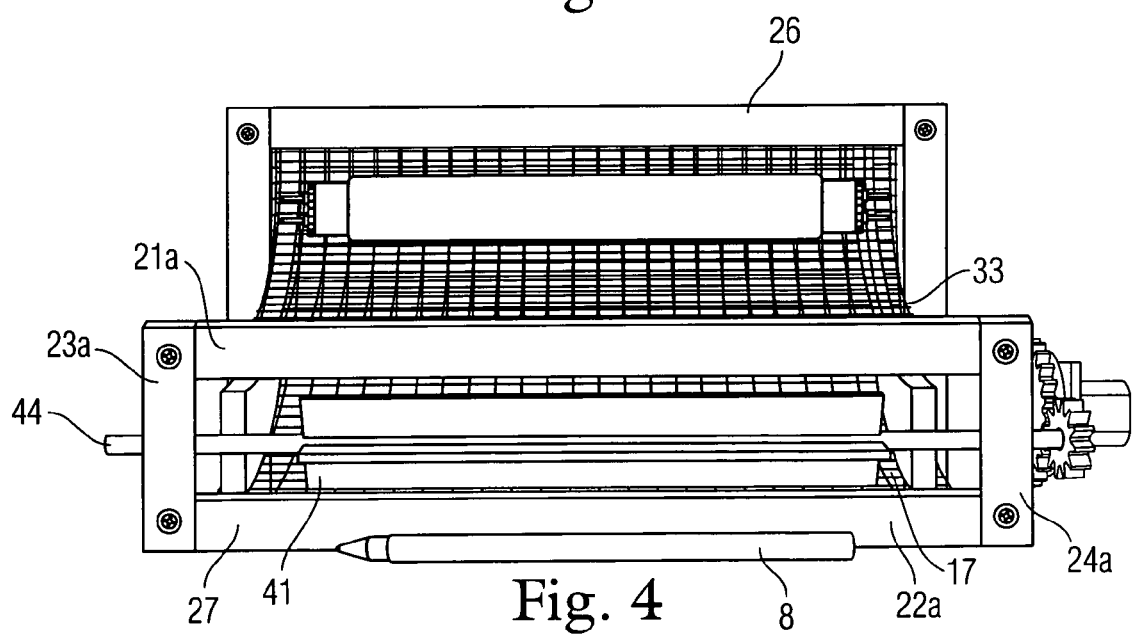
FIG. 4 illustrates a front view of the device in accordance with this invention.

Likewise, FIG. 2 illustrates a collection opening 16 defined by a collection frame 26 and configured with an elongated shape through which a writing instrument 8 may be received. The elongated collection frame 26 may also be rectangular in shape including an upper longitudinal member 21b, a lower longitudinal member 22b, and a pair of side members 24b, 25b.

FIGS. 1-4 illustrate a track 30, constructed in a downward sloping incline, extending between the collection opening 16 and the discharge opening 17. In use, writing instruments 8 are individually inserted into the collection opening 16. Under the force of gravity, the writing instrument 8 will traverse along the track 30 from the collection opening 16 to the discharge opening 17.

A cross-section of the track 30 is contiguous and elongated in shape, similar in shape to the elongated collection opening 16 and the elongated discharge opening 17. The track 30 provides openings to allow for UV radiation light 34 to emanate through the track 30 and directly contact all of the surfaces of the writing instrument 8 as it travels from the collection opening 16 to the discharge opening 17. The track 30 may be constructed of mesh, such as wire mesh, or with a structure which varies the location of support to optimize UV exposure and prevent voids, blinds spots, or shielded locations. The structure of the track may be a wire mesh with staggered openings, alternating patterns, or may use wire mesh placed on an angle to provide complete exposure of the UV light 34 on the writing instruments 8.

The track 30 includes at least a guided bottom track 32 upon which the writing instrument 8 may be lead and/or guided from the elongated collection opening 16 to the elongated discharge opening 17 under the force of gravity. As shown, an upper track 33 is also provided to further guide the writing instrument 8 to the elongated discharge opening 17. As the writing instruments 8 compile against each other on the track 30 they are incrementally rotated as the next or each writing instrument is discharged from the discharge opening 17. Through this incremental rotation of the writing instruments the exterior surfaces of the writing instruments are exposed to the UV light. The elongated cross-section of the track 30 is constructed to permit the selective passage of preferably one writing instrument 8 at a time (i.e. next to each other), so as to prevent the writing instruments 8 from overlapping each other (i.e. stacking), thereby interfering with direct contact of the UV light 34 on any one of the writing instruments 8. The track 30 may be formed of any suitable material so that the writing instruments 8 carried therein may be visible to the UV light 34.

FIGS. 34 depict an ultraviolet (UV) light 34 provided to sterilize the writing instruments. Although only one UV light 34 is shown in FIG. 1, it is understood that numerous UV lights 34 may disposed within the housing 80 (shown in FIG. 9) of the writing instrument sterilizer 10. UV radiation is a form of electromagnetic radiation that contains measurable wavelengths in the 4-400 nanometer range. UV radiation is a well-known sterilization agent. The ultraviolet light is effective at eradicating bacteria, viruses and other pathogens. The exposure to UV light necessary to kill bacteria (or the "kill" factor) is a product of time and intensity. Suitable wavelengths for sterilizing a writing instrument 8 are in the range of 100-300 nanometers. The ideal UV germicidal wavelength is approximately 254 nanometers.

However, it is also understood that exposure to UV light at an intensity necessary for effective and efficient eradication or sterilization of pathogenic agents is harmful to the human body so appropriate protective shielding is utilized within the dispenser to prevent direct or reflected UV light from striking the human body. The UV radiation required to effectively eradicate most pathogenic agents will be an intensity ranging from 1000-100,000 microwatts/cm$^2$ with an ideal range of 3,000-10,000 microwatts/cm$^2$. The object of this invention is to effectively eradicate pathogens or micro-organisms by exposing all surfaces of the writing instrument to direct (or reflected) exposure or contact with the UV radiation for a sufficient period of time. According to this exemplary embodiment, a predetermined time period for applying UV radiation to effectively sterilize the writing instruments 8 has been calculated in the range of 30-240 seconds. Ideally, the UV radiation exposure time period when using a UV light with a wavelength of approximately 254 nanometers at an intensity of 10,000 microwatts/cm$^2$ is in the range of 80-110 seconds. However, the time may vary based on the internal surface area, the internal reflective material used, and the radiation level and/or wattage output of the UV lamp 34.

Various types of illumination lamps may be employed, such as for example, an UV light, a pulsed or flashed UV light, a germicidal UV flash light or LED (light emitting diodes), pulsed UV and/or any other disinfecting illumination source now known or later discovered in accordance with this invention. Ideally, the present invention will include a UV lamp which produces UV light wavelengths of approximately 254 nanometers.

To further ensure that only one of the writing instruments 8 is permitted to exit the discharge opening 17 at one time, the present invention includes a single writing instrument dispensing assembly 40.

Figure 5:
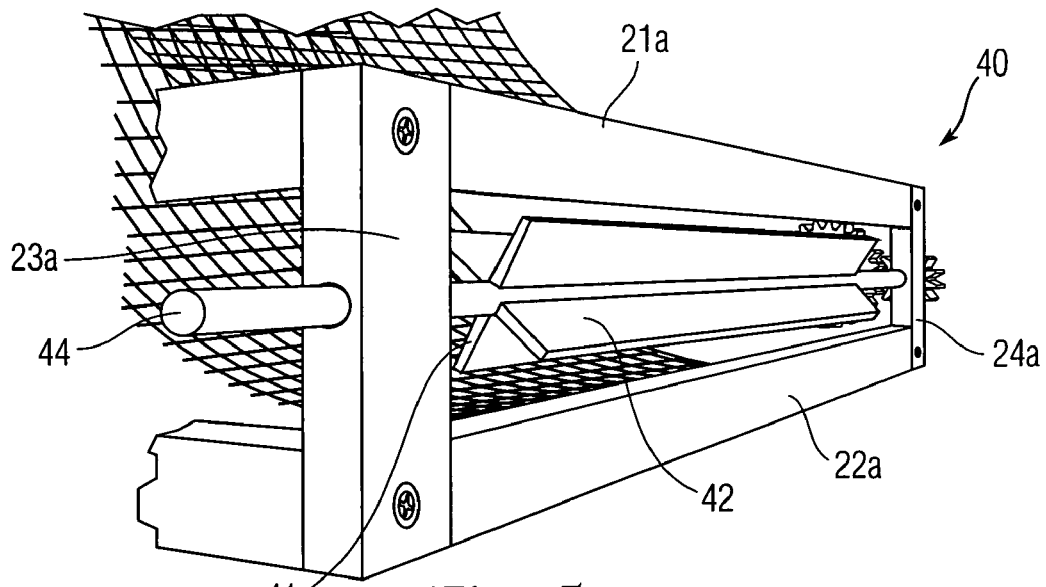
FIG. 5 illustrates a perspective view of the left end of the device in accordance with this invention.
Figure 6:
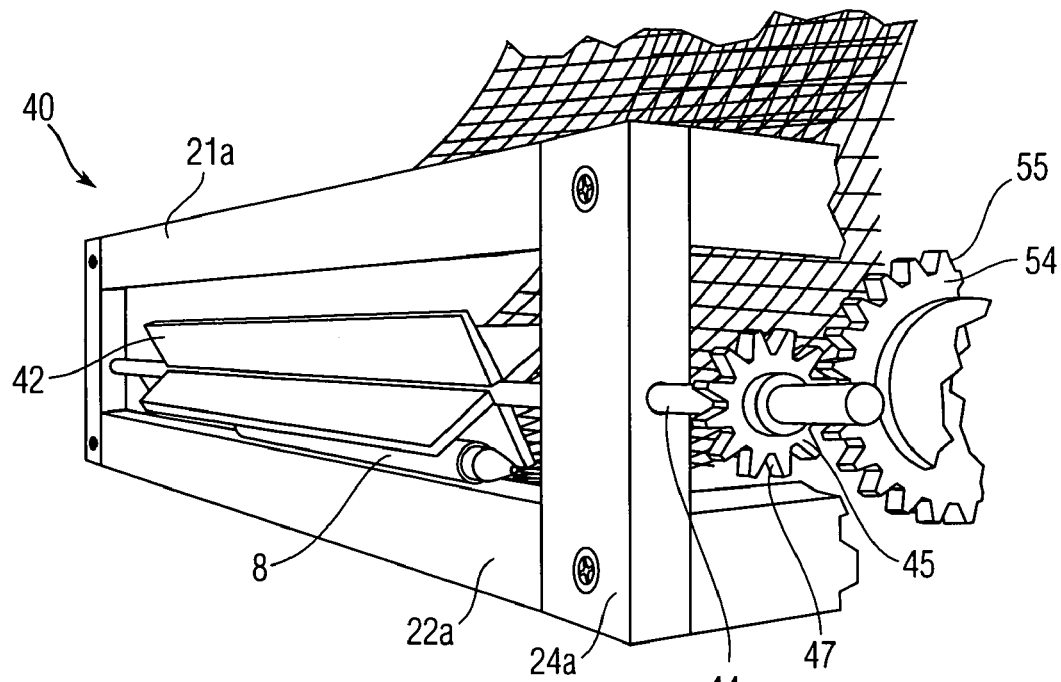
FIG. 6 illustrates a perspective view of the right end of the device with the carriage in an implement engaging position in accordance with this invention.
Figure 7:
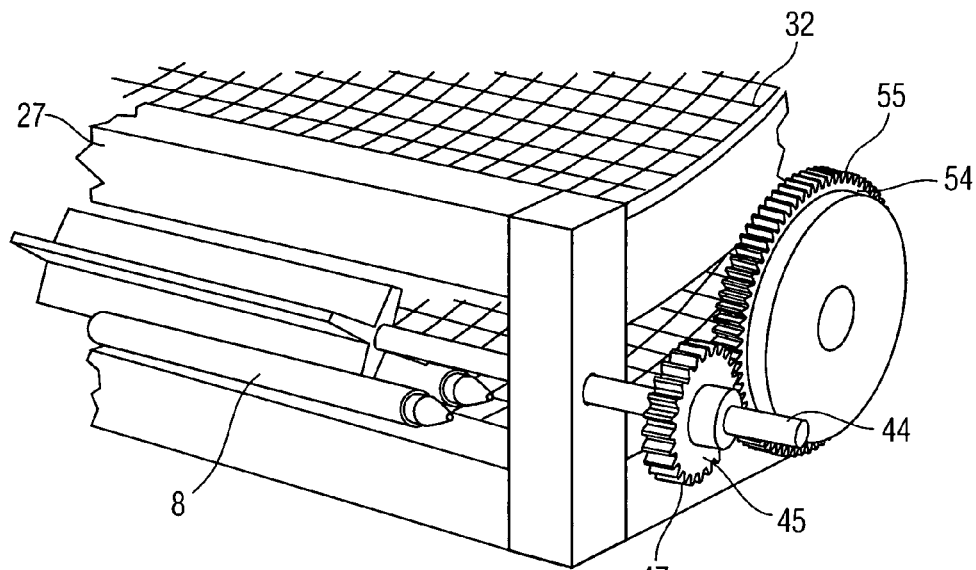
FIG. 7 illustrates a perspective view of the right end of the device with the carriage in an implement delivery and ejection position in accordance with this invention.

FIGS. 4-8 and FIGS. 11-13 depict the writing instrument dispensing assembly 40 in more detail. In particular, the dispensing assembly 40 includes a single writing instrument ejector member 41. As shown in FIGS. 5-7, the ejector member 41 includes an elongated member secured to and extending parallel to an axis of a pivot rod 44.

The ejector member 41 includes a plurality of legs or fins 42 extending radially from pivot rod 44. The legs 42 are radially located around the pivot rod 44 so that a gap 43 is formed between two adjacent legs 42. The gap 43 formed is just large enough to permit entry of one writing instrument 8 within the gap 43 when the ejector member 41 is rotated from a first writing instrument 8 receiving position to a second writing instrument 8 discharging position.

In position, the ejector member 41 is disposed in at least a partially covered relation over the elongate slot of the discharge opening 17 so that unless the ejector member 41 is rotated from a first closed receiving position to an second discharging position, a writing instrument 8 within the track 30 will not pass through the elongate discharge opening 17 and out of the writing instrument sterilizer 10.

In particular, the pivot rod 44 is longitudinally disposed along the discharge opening 17, and pivotally braced by the discharge frame 27. At a first end the discharge frame 27, the pivot rod 44 is pivotally journaled to side member 23*a*. At a second end the discharge frame 27, the pivot rod 44 is pivotally disposed through the side member 24*a* and coupled to a drive motor 50.

Figure 8:
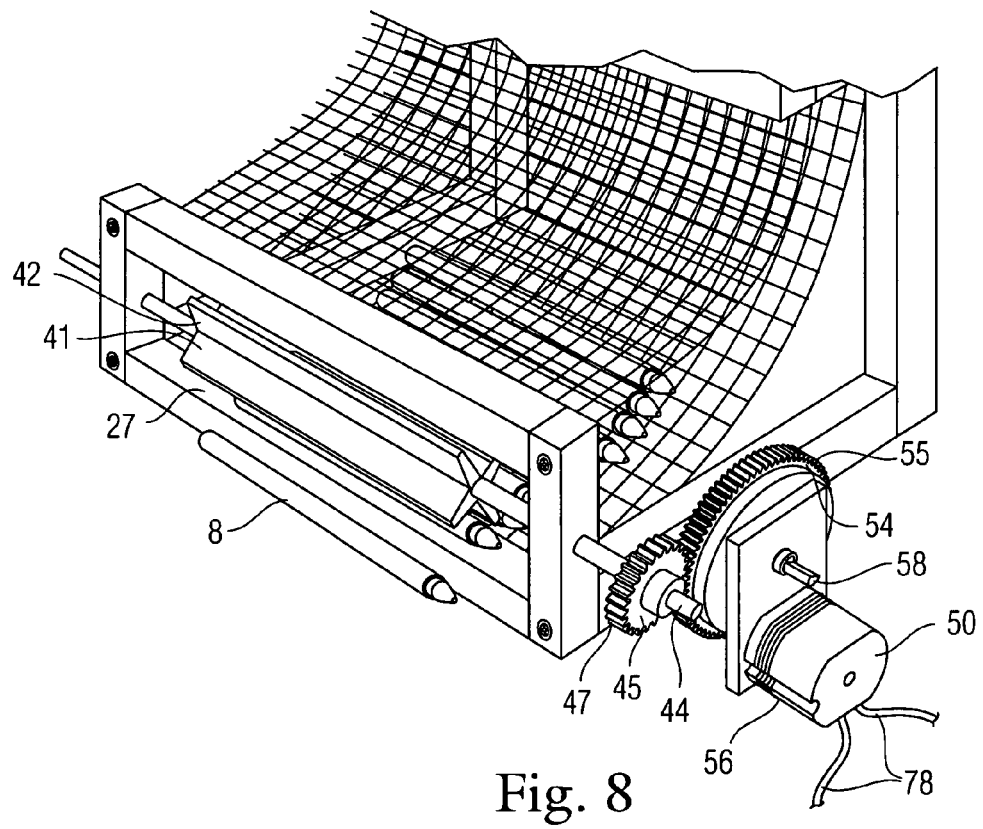
FIG. 8 illustrates a perspective view of the motor driving the delivery mechanism in accordance with this invention.

FIGS. 7-8 illustrate the drive motor 50 of the automatic dispensing assembly 40. The exemplary drive motor 50 depicts a power supply being supplied through wires 78 to an actuation assembly 56 constructed to rotate the ejector member 41. The drive motor 50 includes a drive motor output shaft 58 with a drive gear 54 having a plurality of drive gear teeth 55. The drive gear teeth 55 matingly engage a plurality of slave gear teeth 47 of a slave gear 45. The slave gear 45 is fastened to the pivot rod 44.

Figure 11:
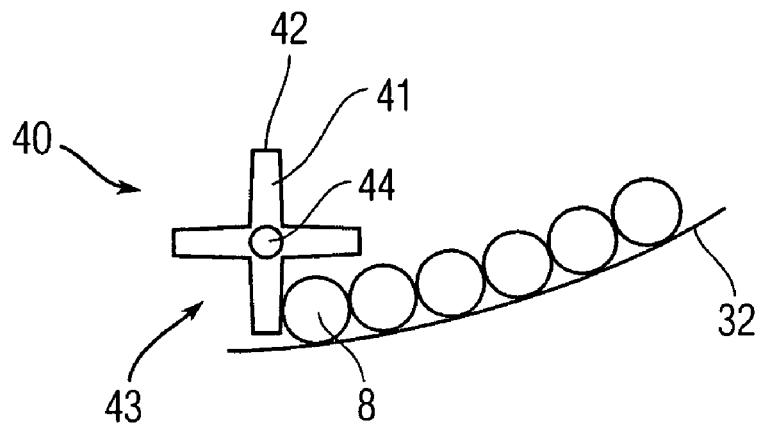
FIGS. 11-13 depict the ejector member rotating though a cycle and dispensing a writing instrument in accordance with this invention.
Figure 12:
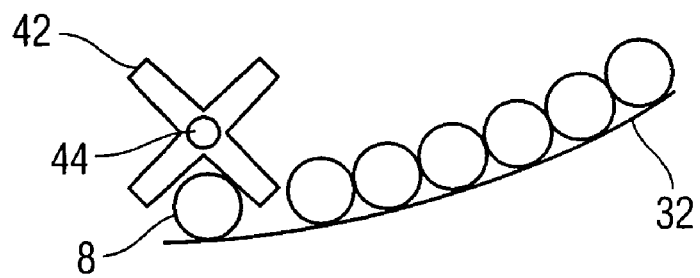
Figure 13:
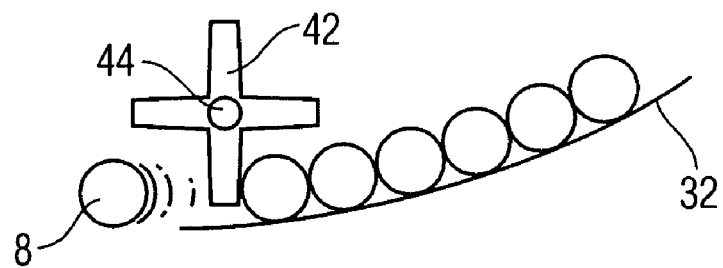

In operation, when the drive motor 50 is actuated, rotation of the drive gear 54 causes the slave gear 45 to rotate the pivot rod 44 which urges the ejector member 41 to move from the first writing instrument 8 receiving position (as shown in FIG. 11) through an intermediate position (as shown in FIG. 12) to a second instrument dispensing position (as shown in FIG. 13). In particular, the ejector member 41 is radially driven from a first closed impasse position (as shown in FIG. 11) in which a writing instrument 8 is received, to an intermediate position in which the writing instrument is urged outward towards the discharge opening 17 against the lower track 32 (as shown in FIG. 12) to a second discharge position (as shown in FIG. 13) in which the writing instrument 8 is shown being ejected through the discharge opening 17 and away from the writing instrument sterilizer 10.

As will be described later, the drive motor 50 can be actuated in a variety of different ways, including but not limited to, being actuated by a controller connected to a variety of actuation and/or detection devices. As described above, the mode for dispensing a writing instrument 8 is done automatically in response to a control signal initiated from at least one of various actuation (and/or detection devices). The control signal is received by the processor 70 (or controller), which in turn automatically dispenses a sterilized writing instrument 8.

Although described as an automated writing instrument sterilizer 10, it is also understood that the dispensing of a writing instrument 8 may be mechanically and/or semi-mechanically performed. That is, a variety of actuation methods for dispensing the writing instrument 8 are possible, including but not limited to, providing a lever (not shown) that pivots. For example, the lever may be connected to an eccentrically weighted distributed ejector member 41, so that when pressure is applied to displace the lever, the ejector member 41 is urged from a radial stop position to a writing instrument 8 dispensing position. When the pressure to the lever is released, the ejector member 41 may normally return to its radial stop position in which the writing instruments 8 are blocked from exiting the discharge opening 17.

Various modes for defining a radial stop position may be implemented, such as for example, using a pin (not shown) to limit rotational movement of ejector member 41 between a stop position in which the writing instrument 8 is received by the ejector member 41 to a dispensing position in which the writing instrument 8 is ejected from the discharge opening 17.

Figure 9:
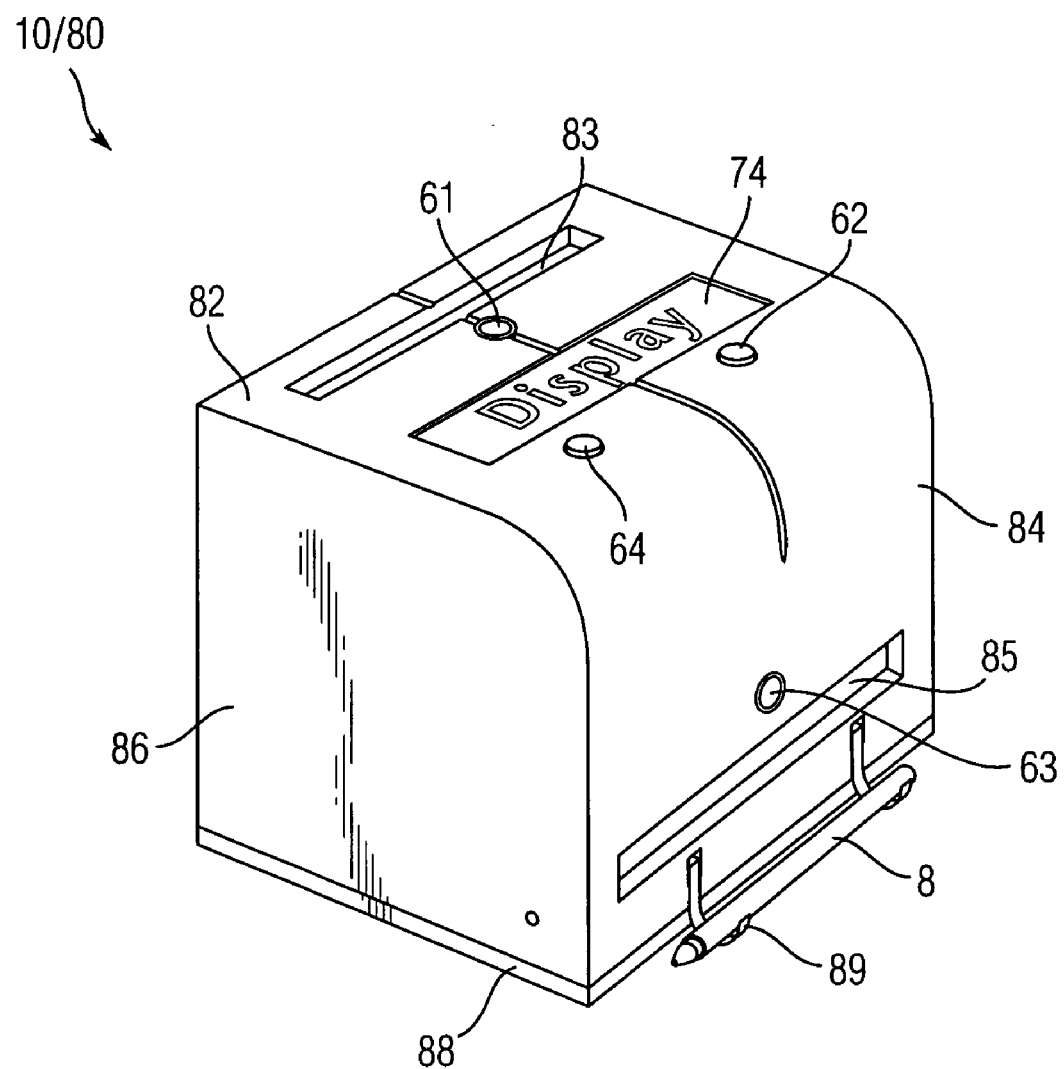
FIG. 9 illustrates a perspective view of the device housed in a container in accordance with this invention.

FIG. 9 depicts an exemplary housing 80 for the writing instrument sterilizer 10. The housing 80 includes a collection panel 82, a discharge panel 84, various other side panels 86 and a base panel 88. The housing 80 is preferably lined with a reflective material (not shown), such as for example, a metallic laminate and/or any other material having suitable reflective properties to reflect the irradiating light from the UV light 34 back toward the surfaces of the writing instruments 8 within the housing 80 of the writing instrument sterilizer 10 in order to maximize the exposure to the various writing instruments 8.

The collection panel 82 includes an elongated collection aperture 83 that is aligned over the collection opening 16 in the collection frame 26. As shown, a display 74 and various buttons and/or sensors are shown disposed on the collection panel 82. As will be described later in more detail, a dispensing switch 62 and an illumination switch 64 are shown disposed on the collection panel 82. In addition, as previously described motion sensors 61, 63 may be employed which sense motion to begin the sterilization process when motion is sensed by sensor 61 or to dispense a sterilized writing instrument when motion is sensed by sensor 63.

The discharge panel 84 includes an elongated discharge aperture 85 that is aligned over the discharge opening 17 in the discharge frame 27. The discharge panel 84 also includes a receiving element 89 for receiving the writing instrument 8 dispensed from the writing instrument sterilizer 10. The receiving element 89 may be constructed from a variety of different collection devices. For example, the receiving element 89 may be embodied as a shelf, a tray, a pair of of hooks, and/or any other mechanism for receiving a sterilized writing instrument 8. Further, the receiving element 89 may also be a mechanical lever for mechanically turning the ejector member 41 or to act as a switch to activate the motor 50 for turning the ejector member 41 to dispense a sterilized writing instrument 8 or to initiate a sterilization process.

Although FIG. 9 depicts a collection panel 82 including an elongated collection aperture 83 for receiving a writing instrument 8, and a discharging panel 84 including an elongated discharge aperture 85 for dispensing a writing instrument 8, it is to be understood that the structure of the writing instrument sterilizer 10 may be modified so that a single elongated aperture is provided in the housing 80 for both receiving and dispensing a writing instrument 8.

Figure 10:
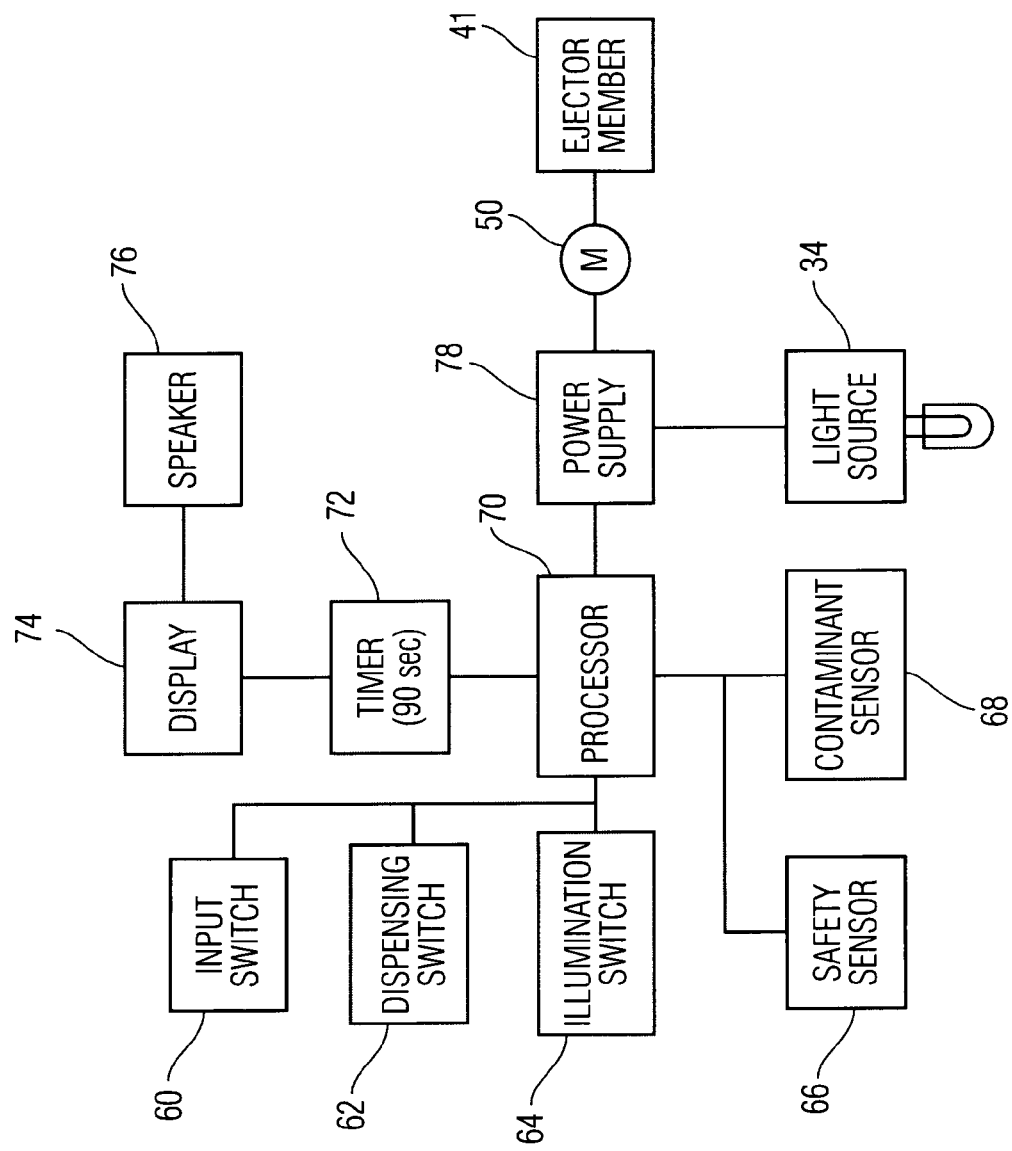
FIG. 10 illustrates a control circuit for the writing instrument sterilizer in accordance with this invention.

FIG. 10 illustrates a control circuit for the writing instrument sterilizer 10 according to this invention. In operation, a user may insert a writing instrument 8 into the collection opening 16. An input switch input switch 60 may be located at the opening of the collection opening 16. When the writing instrument 8 is inserted into the collection opening 16, a processor 70 receives a signal indicating the receipt of a new writing instrument 8. The processor 70 transmits a control signal to the power supply 78 to provide a source of power to the UV light 34 thereby allowing the various writing instruments 8 within the writing instrument sterilizer 10 to be sterilized by the irradiating UV light 34.

Within the control circuit, the writing instrument sterilizer 10 may include a timer 72 to measure a predetermined period of time that the UV light 34 irradiates the writing instrument 8. A preferred predetermined period of time has been determined to be approximately 90 seconds in accordance with this exemplary embodiment. However, it is to be understood that the predetermined time may vary based on a variety of different parameters, such as the UV light bulb, the size of the housing, the reflective properties of the inner housing surfaces, the design of the track 30, the writing instruments 8 within the housing 80 and/or other variables.

The timer 72 may be connected to a display 74 or speaker 74. When the writing instrument 8 has been sufficiently sterilized a visual notification may be displayed on display 74 and/or an audible sound may be emitted through a speaker 76 indicating to the user that the sterilization process is complete.

The writing instrument sterilizer 10 may be connected to a contamination sensor 68 which senses and determines whether the writing instrument 8 is sufficiently sterilized. If the contamination sensor 68 indicates that the writing instruments 8 are not sufficiently clean, the processor 70 will continue to instruct the power supply 78 to generate the UV light 34 until the contamination sensor 68 indicates a sterilized environment.

In more detail, the contamination sensor 68 may be used to determine properties of the surface to be treated. Information of interest can include surface type, hardness, texture, reflectivity, and/or the extent of dirt and/or contaminants. Various other sensors, such as optical sensors, contact sensors, can be used to gather the information. The control circuit can give an indication of the surface properties and the information from the contamination sensor 68 can be communicated to the processor 70 and used in a pre-programmed algorithm to adjust the UV intensity to be specifically tuned for the surface being treated. In the alternative, it may indicate that the UV light 34 should be moved closer to the surface of the writing instrument 8 and/or the UV intensity should be reduced.

The writing instrument sterilizer 10 may include safety sensors and interlocks (hereafter safety sensor 66) that shut off the UV light 34 when an unsafe condition is detected. An unsafe condition may include where a UV light 34 is directed away from the treatment surface and/or in directions where it can irradiate people or animals. If an unsafe situation should occur, the processor 70 will receive control signals from the safety sensor 66 noting the harmful environment, and the processor 70 will instruct the power supply 78 to cease its supply of power to the UV light 34.

In addition to the safety sensor or sensors 66, the design of the enclosure also prevents the escape of UV light from the enclosure. The design and location of both the collection aperture 83 and discharge aperture 85 in relation to the UV light 34 as well as the fins 42 of the ejector member 41 help to prevent any UV light from escaping or emitting outside of the enclosure. Further, plastic doors may be attached in a hinged opening fashion to both the collection aperture 83 and discharge aperture 85 to provide additional UV protection.

In the alternative, an illumination switch 64 may be provided on the writing instrument sterilizer 10 which when activated, the processor 70 will instruct the irradiation of the UV light 34 until the inner compartment of the writing instrument sterilizer 10 is sterilized. When it has been determined that the writing instruments 8, are sterilized, the processor 70 will instruct the UV light 34 to cease operation.

The circuit includes controls for the dispensing assembly 40 (as referred to in FIGS. 7-8). The ejector member 41 may be controlled in a variety of different ways, including in response to a dispensing switch 62 and/or the input switch 60. If, for example, the dispensing switch 62 is activated, in response to the signal communicated to the processor 70, the processor 70 will instruct the power supply 78 to provide a source of power to motor 50 to drive the ejector member 41 through a cycle which would dispense a writing instrument 8.

The dispensing switch 62 may be embodied in a variety of different ways. For example, the dispensing switch 62 may be employed as a motion or proximity switch, such that if the user motions his hand contemporaneously close to the dispensing switch 62 or motion sensor 63 proximate the discharge aperture 85 located outside of the writing instrument sterilizer 10, the circuit will receive a control signal to dispense a writing instrument 8. The dispensing switch 62 may also be a touch sensor, a weight or location controlled switch working in conjunction with the sterilized pen holder or receiving element 89, a button that may be repressed and/or any other mode for activating a switch now known or later discovered in accordance with this invention. In the preferred embodiment, the present invention is able to determine that a sterilized writing instrument 8 is not available in the receiving element 89 and automatically provides a new sterilized writing instrument 8 to the receiving element 89 as a way of promoting the sterilization and recycling process of writing instruments 8.

In the alternative, the ejector member 41 may be instructed to cycle once and dispense a writing instrument 8 in response to activation of the input switch 60. For example, if activation is sensed when a writing instrument 8 is inserted into the collection opening 16 or through motion sensor 61, the processor 70 may issue an instruction to cycle the ejector member 42 to dispense a writing instrument 8. The writing instrument 8 may be dispensed before or after the UV light 34 is activated to irradiate the various writing instruments 8. If, however, the only writing instrument 8 in the writing instrument sterilizer 10 is the one recently deposited, the processor 70 will sterilize the writing instrument 8 before it is dispensed for use.

It should be noted that the processor 70 may be preferably implemented as a central processor section having overall, system-level control, to performing various computations, functions and other processes related to the writing instrument sterilizer 10. The various components in the control circuit associated with the processor 70 can be implemented as a single microprocessor circuit or a plurality of separate dedicated or programmable integrated or other electronic circuits or devices, e.g., hardwired electronic or logic circuits such as discrete element circuits or programmable logic devices. The control circuit may include other circuitry or components, such as memory devices, relays, mechanical linkages, communications devices, etc., to affect desired control and/or input/output functions from various interfaces, such as where the display 74 shown in FIG. 9 is an input/output interface. The writing instrument sterilizer 10 may include more than one controller for the various electronic components in accordance with this invention.

Programmable memory may be provided to receive and store the various data information and can also store one or more computer readable control routines used by the processor 70 to operate the writing instrument sterilizer 10. The memory can be implemented using any appropriate combination of alterable, volatile or non-volatile memory or non-alterable, or fixed, memory. The alterable memory, whether volatile or non-volatile, can be implemented using any one or more of static or dynamic RAM, floppy disk and disk drive, writable or re-writable optical disk and disk drive, hard drive, flash memory or the like. Similarly, the non-alterable or fixed memory can be implemented using any one or more of ROM, PROM, EPROM, EEPROM, an optical ROM disk, such as CD-ROM or DVD-ROM disk, and disk drive or the like.

It will be recognized by those skilled in the art that changes or modifications may be made to the above described embodiment without departing from the broad inventive concepts of the invention. It is understood therefore that the invention is not limited to the particular embodiment which is described, but is intended to cover all modifications and changes within the scope and spirit of the invention.

What is claimed is:

1. A writing instrument sterilizer, comprising:
    a housing comprising a collection aperture configured to receive at least one writing instrument and a discharge aperture configured to dispense the writing instrument;
    a track disposed within the housing that extends between the collection aperture and the discharge aperture upon which the writing instrument is transferred, wherein at least a portion of the track slopes downward from the collection aperture;
    an illumination source that sterilizes the writing instrument by emitting radiation to the surface of the writing instrument; and
    an automatic delivery mechanism operable to move an ejector member configured to move the writing instrument from a first instrument receiving position to a second instrument dispensing position.

2. The writing instrument sterilizer as recited in claim 1, further comprising a top panel, a bottom panel and side panels.

3. The writing instrument sterilizer as recited in claim 1, wherein the writing instrument is conveyed under the force of gravity.

4. The writing instrument sterilizer as recited in claim 1, wherein the track is comprised of a bottom track having a guide which guides the writing instrument from the collection aperture to the discharge aperture and prevents more than one writing instrument from overlapping with an adjacent writing instrument.

5. The writing instrument sterilizer as recited in claim 1, wherein a cross-section of the track between the collection aperture and the discharge aperture is a substantially continuous elongated shape constructed to permit the passage of one writing instrument while preventing the writing instruments from overlapping with each other.

6. The writing instrument sterilizer as recited in claim 1, wherein the illumination source is irradiated to all surfaces of the writing instrument for a predetermined period of time sufficient to completely sterilize the writing instrument.

7. The writing instrument sterilizer as recited in claim 1, wherein internal surfaces of the housing are reflective to reflect the radiation from the illumination source to the surface of the writing instrument.

8. The writing instrument sterilizer as recited in claim 1, wherein the automatic delivery mechanism comprises an ejector member that rotates from the first instrument receiving position to the second instrument dispensing position.

9. The writing instrument sterilizer as recited in claim 8, wherein the ejector member longitudinally extends along, and is fastened to, an axis of a pivot rod disposed in at least a partially covered relation over the elongate slot of the discharge aperture.

10. The writing instrument sterilizer as recited in claim 8, further comprising a frame including a collection opening connected to a discharge opening by a pair of vertical support members connected to a pair of base support members,
    wherein the collection opening is defined by an elongated collection frame comprising an upper longitudinal member, a lower longitudinal member, and a pair of side members; and
    wherein the discharge opening is defined by an elongated discharge frame comprising an upper longitudinal member, a lower longitudinal member, and a pair of side members.

11. The writing instrument sterilizer as recited in claim 10, wherein the pivot rod is pivotally braced by the discharge frame, and wherein at a first end, the pivot rod is pivotally journalled to a first side member of the discharge frame and at second end of the discharge frame, the pivot rod is pivotally disposed through the second side member of the discharge frame and coupled to a drive motor.

12. The writing instrument sterilizer as recited in claim 1, wherein the ejector member includes a plurality of legs extending radially outward from the pivot rod so that a gap formed between two adjacent legs is large enough to permit entry of one writing instrument within the gap such that when the drive motor is actuated, the pivot rod rotates in a first direction thereby radially driving the ejector member from the first instrument receiving position to the second instrument dispensing position.

13. The writing instrument sterilizer as recited in claim 1, wherein the automatic delivery mechanism includes a drive motor having a drive motor output shaft with a drive gear whose drive gear teeth are matingly engaged with slave gear teeth of a slave gear fastened to the pivot rod, wherein when the drive motor is actuated, rotation of the drive gear urges the rotation of the slave gear so that the pivot rod urges the ejector member to move from the first instrument receiving position to the second instrument dispensing position.

14. The writing instrument sterilizer as recited in claim 13, wherein the drive motor is actuated in response to detection of a moving object in close relation to a dispensing switch.

15. The writing instrument sterilizer as recited in claim 14, wherein the drive motor is actuated in response to activation of at least one Of an input switch and an illumination switch.

16. The writing instrument sterilizer as recited in claim 1, wherein illumination of the light source is halted in response to receipt of a control signal from a safety sensor.

17. The writing instrument sterilizer as recited in claim 1, wherein illumination of the light source is continued until a contaminant sensor has issued a control signal indicative of the surface of the writing instrument to be dispensed being contaminant free.

18. A writing instrument sterilizer, comprising:
    a housing comprising a collection aperture configured to receive at least one writing instrument and a discharge aperture configured to dispense the writing instrument;
    a track disposed within the housing that extends between the collection aperture and the discharge aperture upon which the writing instrument is transferred, wherein at least a portion of the track slopes downward from the collection aperture
    a controller that controls a circuit for sterilizing and dispensing of the writing instrument, comprising:

an illumination source that sterilizes the writing instrument in response to an instruction from the controller to emit radiation to the surface of the writing instrument; and an automatic delivery mechanism operable to move an ejector member configured to move a writing instrument from a first instrument receiving position to a second instrument dispensing position in response to an instruction from the controller.

19. The writing instrument sterilizer as recited in claim 18, wherein the controller instructs the drive motor to be actuated in response to a control signal received from a dispensing switch that detected movement of an object in close relation to the dispensing switch.

20. The writing instrument sterilizer as recited in claim 18, wherein the controller instructs the drive motor to be actuated in response to a control signal received from at least one of an input switch and an illumination switch.

21. The writing instrument sterilizer as recited in claim 18, wherein the controller instructs the light source to halt operation in response to a control signal received from a safety sensor.

22. The writing instrument sterilizer as recited in claim 18, wherein the controller instructs the light source to continue to illuminate a sterilizing dosage of radiation to the writing instrument in response to a control signal received from contaminant sensor indicating that the surface of the writing instrument is not substantially contaminant free.

23. A writing instrument sterilizer, comprising:
a housing comprising a collection aperture configured to receive at least one writing instrument and a discharge aperture configured to dispense the writing instrument;
a track disposed within the housing that extends between the collection aperture and the discharge aperture upon which the writing instrument is transferred, wherein at least a portion of the track slopes downward from the collection aperture
a controller that controls a circuit for sterilizing and dispensing of the writing instrument, comprising:
an illumination source providing ultraviolet light at a wavelength of approximately 254 nanometers for sterilizing the writing instrument in response to an instruction from the controller to emit radiation with an intensity range of 1000-100,000 microwatts/cm$^2$ to the surface of the writing instrument; and
an automatic delivery mechanism operable to move an ejector member configured to move the writing instrument from a first instrument receiving position to a second instrument dispensing position in response to an instruction from the controller.

* * * * *